United States Patent [19]

Noguchi et al.

[11] 4,416,783
[45] Nov. 22, 1983

[54] LIQUID CHROMATOGRAPHY COLUMN, PROCESS FOR PREPARING THE SAME AND ITS USE FOR FRACTIONATION

[75] Inventors: Kohji Noguchi; Masao Kasai, both of Yokohama, Japan

[73] Assignee: Asahi Kasei Kogyo Kabushiki Kaisha, Osaka, Japan

[21] Appl. No.: 341,040

[22] Filed: Jan. 20, 1982

[30] Foreign Application Priority Data

Feb. 12, 1981 [JP] Japan .................................. 56-17985

[51] Int. Cl.³ ............................................ B01D 15/08
[52] U.S. Cl. ................................ 210/635; 210/198.2; 210/927
[58] Field of Search ..................... 210/635, 656, 198.2, 210/927

[56] References Cited

U.S. PATENT DOCUMENTS

| | | | |
|---|---|---|---|
| 3,586,626 | 6/1971 | Heitz | 210/635 |
| 4,016,149 | 4/1977 | Travis | 210/635 |
| 4,094,833 | 6/1978 | Johansson et al. | 210/635 |
| 4,338,404 | 7/1982 | Tanaka | 210/635 |
| 4,339,500 | 7/1982 | Yanagihara et al. | 210/198.2 |
| 4,353,801 | 10/1982 | Mukoyama et al. | 210/198.2 |

OTHER PUBLICATIONS

Introduction to Modern Liquid Chromatography by Snyder et al., John Wiley & Sons, N.Y., N.Y., pp. 187–194, Pub. 1974.
Japanese Kokai No. 52-138077 dated Nov. 17, 1977.
Japanese Kokai No. 53-60290 dated May 30, 1978.
Heitz J. Chromatography 53, (1970), 37–49.

*Primary Examiner*—John Adee
*Attorney, Agent, or Firm*—Sprung, Horn, Kramer & Woods

[57] ABSTRACT

A liquid chromatography column comprising a uniform gel bed of a high packing ratio, which is produced by a process in which a column is prepared while avoiding imposing an abrupt change of flow rate or pressure on the gel bed during the column packing operation, thereby making it possible to simultaneously improve the elution speed and the durability of the column. The column comprises gels of small grain diameter, thereby exhibiting an excellent resolution. The column also ensures a direct analysis of blood serum.

18 Claims, 8 Drawing Figures

Rt (min)

FIG.6

LIQUID CHROMATOGRAPHY COLUMN, PROCESS FOR PREPARING THE SAME AND ITS USE FOR FRACTIONATION

This invention relates to a liquid chromatography column comprising totally porous gels containing vinyl alcohol units. More particularly, the present invention is concerned with a high-speed, high-resolution liquid chromatography column comprising a uniform gel bed of a high packing ratio of totally porous gels containing vinyl alcohol units and having high hydrophilicity and improved mechanical strength which is, for a primary aspect, to effect gel permeation chromatography separation using an aqueous eluent, a process for preparing the same and its application method for fractionation. The term "totally porous" as used herein means that fine pores are distributed throughout the grain of the gel. By the term "vinyl alcohol units" is meant a moiety of the formula:

Liquid chromatography permits fractionation of a liquid-form mixture into constituent liquid-form substances thereof while maintaining the liquid state. It is not necessary to gasify samples as opposed to the gas chromatography, and the desired substances can be separated without undergoing any degradation or changes. Therefore, the liquid chromatography is being employed in various fields, such as chemistry, biochemistry and pharmacy. According to the mechanism of separation, the liquid chromatography is classified into the gel permeation chromatography (hereinafter referred to as GPC), partition chromatography, adsorption chromatography, ion exchange chromatography and others.

In accordance with the recent remarkable progress of high-speed chromatography and increased application in various fields, there is a strong demand in the art for an improvement, with respect to efficiency, in an aqueous-solvent GPC column which is used to separate water-soluble solutes from each other according to the molecular sizes thereof by using water or an aqueous solution as eluent.

Of the most widely used of the aqueous-solvent GPC columns are dextran gel- or agarose gel-packed columns. These gels contained in such columns are soft gels and, hence, high-speed analysis is impossible. With respect to "soft gels", reference may be made to UK Patent Application Laid-Open Specification No. GB 2 061 954A. Of the improved-type column as compared to the above-mentioned ones is a polyethyleneglycol dimethacrylate gel-packed column, which is, however, still insufficient with respect to the separating capacity and the flow rate of the eluent.

It was proposed in Japanese Patent Application Laid-Open Specification No. 138077/1977 to use an aqueous gel obtained by saponifying grains of a copolymer of diethylene glycol dimethacrylate or the like with vinyl acetate and cross-linking the saponified copolymer with epichlorohydrin. In this publication, however, there is no description ensuring sufficient separation at a high flow rate. Insufficient separation is due partly to the grain size of the gels being as large as 300 to 400 mesh.

As the column ensuring relatively high-speed analysis and improved separation, there have been proposed columns packed with porous silica gel, the surface of which has been subjected to chemical treatment to prevent adsorption of solutes thereon. In fact, columns of this type are being widely used. However, the skeleton of the gels is inorganic, and hence, it is difficult to control with reproducibility the pore diameter of the gels, which is an important factor of GPC gels, thereby causing the optimum pore diameter range to be narrowed. It is also difficult to attain a high packing ratio of gel bed, thereby causing the durability of the column to be poor. Further, in using the silica gel column, the pH of the eluent applied must be in the range of 3 to 9. Even in this pH range, traces of silica move into the effluent, which adversely affects the chromatographic analysis.

To produce a high-performance packed column, it is a factor of crucial importance in what state the gel bed is formed. Illustratively stated, it is essential that a high packing ratio of gel bed be uniformly formed. In line with this concept, it was proposed in Japanese Patent Application Laid-Open Specification No. 60290/1978 to uniformly mix large grain-size gels and small grain-size ones to give a high packing ratio of gel bed. This process has a drawback that it is inevitably accompanied by an increased "height equivalent to a theoretical plate" (hereinafter referred to as "HETP"), resulting from mingling of large grain-size gels. The "HETP" is defined as that length of column which will yield an effluent in equilibrium with the mean concentration over that length in the stationary phase. The drawbacks of the above-mentioned conventional columns have connection with the inherent nature of the gels and the state of the formed gel bed. Therefore, it is essential to identify the optimum conditions of these factors to complete a high-speed, high-resolution, well durable column.

We have made extensive and intensive studies on the various factors contributing to the efficiency of the packed GPC column, and found the optimum combination of conditions to build a high-speed, high-resolution liquid chromatography column of prolonged durability. Based on this finding, we have completed this invention.

It is, therefore, an object of the present invention to provide an improved liquid chromatography column comprising a uniform bed of a high packing ratio of such gels that do not cause solutes to be adsorbed thereon leading to insufficient separation of components (in other words, have a non-ionic but highly hydrophilic chemical structure), that have the pore size and porosity controlled into the optimum range, and that are in the form of fine grains to ensure high resolution and at the same time hold good mechanical strength to endure high-speed chromatographic analysis.

It is another object of the present invention to provide a process for preparing such an improved liquid chromatography column.

It is a further object of the present invention to provide an analytical method using such an improved liquid chromatography column.

The foregoing and other objects, features and advantages of the present invention will be apparent to those skilled in the art from the following detailed description and appended claims taken in connection with the accompanying drawings in which:

FIGS. 3 (a) and (b) are chromatograms obtained by fractionating human serum (detected by UV absorption at 254 nm) according to Example 3 which will be given later. FIG. 3(a) is that of a normal human serum, and FIG. 3(b) is that of a renal failure serum;

FIGS. 5(a) and (b) are chromatograms obtained by fractionating the renal failure serum (detected by UV absorption at 254 nm) by using the liquid chromatography column according to Example 4 which will be given later. FIG. 5(a) was obtained at a flow rate of 1.0 ml/min, and FIG. 5(b) was obtained at a flow rate of 2.0 ml/min.

In one aspect of the present invention, there is provided a liquid chromatography column comprising a high packing ratio of gel bed of totally porous gels containing vinyl alcohol units and having an average grain diameter of 4 to 20 μm, and wherein the bed has a uniformity degree of 2.0 to 4.0, said uniformity degree being defined by HETP/Dp in which HETP represents the height equivalent to a theoretical plate of the column and Dp represents the weight average grain diameter of the gels.

The gels according to the present invention are cross-linked, totally porous polymer gels and are imparted with sufficient hydrophilicity due to the presence of an appropriate amount of vinyl alcohol units. As aforementioned, by the term "totally porous" is meant a structure of gel in which fine pores are distributed throughout the grain of polymer gel. The rigid gels of such a structure have a large specific surface area in the dry state, generally from 5 to 1,000 m²/g, and they hardly undergo change in pore structure between in the dry state and in the wet state of the gels. With respect to the rigid gel, reference may be made to UK Patent Application Laid-Open Specification No. GB 2 061 954A.

The presence of vinyl alcohol units of the formula may be detected by means of infrared absorption spectroscopy. The desirable content of vinyl alcohol units in the polymer may vary depending on the kind of the solute to be subjected to chromatographic analysis. For example, it should vary between saccharide which is less adsorbable to gels and protein, amino acid or the like which is highly adsorbable to gels. The desirable content of vinyl alcohol units in terms of the concentration of hydroxyl groups is generally from 3 to 15 meq/g, preferably from 4 to 10 meq/g. Other ionic hydrophilic groups, such as carboxyl groups, may be present in the polymer as far as they are present in such an amount as will not cause adsorption of solutes or other adverse effect. The concentration of hydroxyl groups may be determined by reacting the gel containing hydroxyl groups with acetic anhydride in pyridine, and then measuring the amount of acetic anhydride which has been consumed by the reaction with hydroxyl groups. It is expressed by the equivalent weight per gram of the dry gel.

The gels according to the present invention should have a sufficient degree of cross-linking to sustain the fine pore structure and to provide a mechanical strength permitting chromatography at a high flow rate of eluent. The cross-linking part should have a structure resistant to hydrolysis. Preferred gels according to the present invention contain ether linkage, isocyanurate ring or cyanurate ring in the cross-linking part.

With respect to the characteristics of the gels according to the present invention, it is also of importance to control the porosity or water regain (hereinafter referred to as $W_R$). An increase in $W_R$ may be advantageous from the viewpoint of separating capacity, but may be accompanied by the reduction of mechanical strength and/or the formation of a nonuniform gel bed. The $W_R$ value of the gels according to the present invention should generally be in the range of 0.6 to 2.0 ml/g, preferably 0.8 to 2.0 ml/g, more preferably 1.0 to 1.8 ml/g. The use of gels of such a $W_R$ value facilitates formation of a uniform gel bed of high packing ratio and ensures the porosity needed for separation, thus contributing to preparation of a high-speed, high-resolution liquid chromatography column. The $W_R$ value (see Tsuguo Takeuchi and Sadao Mori, "Gel Chromatography", published by Kodansha K.K., Japan in 1972) may be determined by subjecting a dry gel having a weight $W_1$ and sufficiently equilibrated with distilled water to centrifugation at 3,000 rpm at 10° C. for 60 min to remove the water adhering to the surface of the gel, measuring the weight $W_2$ of the gel, and calculating the $W_R$ value according to the following formula:

$$W_R = (W_2 - W_1)/W_1 \quad \text{(ml/g)}.$$

An increase in the grain diameter of the gels in the liquid chromatography column advantageously increases the flow rate of the eluent but disadvantageously decreases the separating capacity. On the other hand, a decrease in the grain size of the gels advantageously enhances the separating capacity but disadvantageously decreases the flow rate of the eluent. The desirable average grain diameter of the gels to be employed in the present invention is in the range of 4 to 20 μm, preferably 6 to 20 μm, more preferably 8 to 15 μm. According to the present invention, the column is packed with relatively small-diametered grains of gels to maximize the separating capacity. In addition, increase of the flow rate of the eluent is attained by formation of a high packing ratio of gel bed. Hence, the column according to the present invention satisfies the above-mentioned two requirements, namely, high resolution and high speed. The weight average grain diameter (hereinafter referred to as "Dp") of the gels is measured by using "Coulter Counter" (trade name of an apparatus manufactured and sold by Coulter Electronics Inc., U.S.A.). The Dp value is calculated according to the following formula:

$$Dp = \Sigma nd^4 / \Sigma nd^3$$

wherein d represents the grain diameter, and n is the frequency of occurrence of the grain diameter.

Besides the above-mentioned Dp, the grain diameter distribution is to be considered as a parameter affecting the permissible flow rate of the eluent. The grain diameter distribution, as defined by weight average grain diameter (Dp) divided by number average grain diameter (Dn), for the column according to the present invention, is recommended to be 1.5 or less, preferably 1.2 or less. The number average grain diameter (Dn) is calculated according to the following formula:

$$Dn = \Sigma nd/\Sigma n$$

wherein n and d are as defined above.

Figure 1:
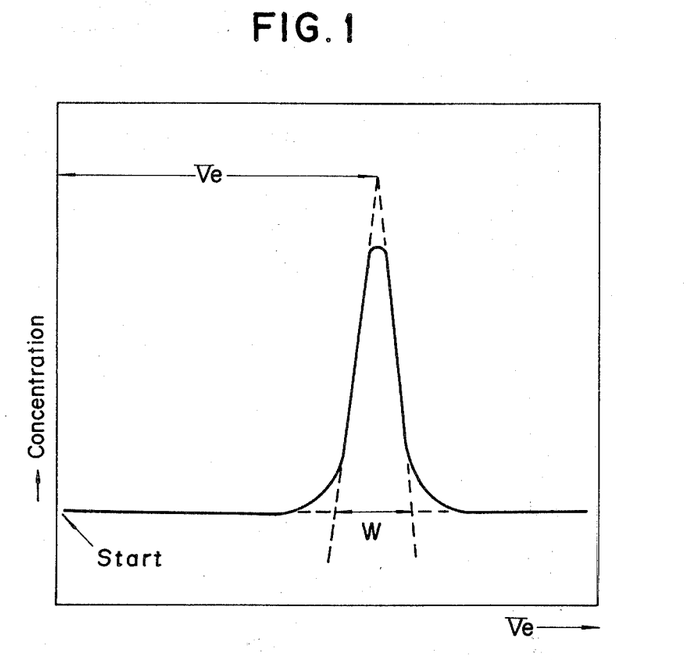
FIG. 1 is a chart showing how to obtain Ve (peak elution volume as defined later) and W (peak width as defined later) based on which the HETP is calculated.

A relative criterion of the uniformity degree of the gel bed is given by the "reduced height equivalent to a theoretical plate" defined as HETP/$D_p$. Herein, HETP is determined by effecting chromatography under predetermined conditions of chromatography with respect to each GPC column of varied kind because HETP's values become different when the conditions of chromatography, such as the flow rate of the eluent or the kind of the solute, are varied. As a result of our study, it was found that an extremely nonuniform gel bed is formed according to the conventional constant-pressure packing method in which a gel slurry is at a time fed into the column by using a high-pressure pump. In the column packed according to this conventional packing method, the portion of the gel bed on the outflow rate of the liquid for packing exhibits an extremely high value of HETP/Dp as compared with other portions of the gel bed. Until the packing ratio of the gel bed as defined later is about 0.6, it is possible to form a relatively uniform gel bed according to the conventional constant-pressure packing method. However, if the packing ratio of the gel bed is further increased, the non-uniformity degree of the gel bed markedly increases. In order to solve this problem, study has been made with respect to both the characteristics of the gel and the preparation technique of the column, and, as a result, a uniform gel bed of a high packing ratio has successfully been developed according to the present invention. The HETP/Dp of the column according to the present invention is in the range of 2.0 to 4.0, preferably 2.5 to 3.5. If the HETP/Dp is greater than 4.0, the resolving capacity of the column markedly drops. If the HETP/Dp is below 2.0, the column is expected to exhibit a high resolving capacity, but it becomes very difficult to prepare the column with reproducibility. The HETP takes different values depending on the chromatography conditions, such as the type of the eluent used and the kind of the solute. The HETP as used herein is determined by conducting chromatography of aqueous 1% by weight ethylene glycol using distilled water as eluent at 25° C. at a flow rate of eluent of 1.5 m/hr (superficial velocity in a column), reading the peak elution volume (Ve) and the peak width (W) from the obtained chromatogram (detected by refractometry) as illustrated in FIG. 1 appended (see Tsuguo Takeuchi and Sadao Mori, "Gel Chromatography", published by Kodansha K.K., Japan in 1972), and calculating the HETP value according to the following formula:

$$HETP = L(W/4\ Ve)^2$$

wherein L represents the length of the column.

The packing ratio of the gel bed in the column according to the present invention should be controlled in association with the $W_R$. By such control, it becomes possible to attain a high packing ratio without impairing the HETP/Dp. Providing that Vt represents the total volume of the column, Vg the volume of the gel substrate, Vi the inner volume of the gel grain, and Vo the void volume between the gel grains, it is known that there is a relationship of Vt=Vo+(Vi+Vg) for the gel packed column. The packing ratio (hereinafter referred to as Pd) of the column according to the present invention is expressed as:

$$Pd = 1 - (Vo/Vt).$$

To calculate Vo, Vi is obtained by multiplying the dry weight of gel (a) and $W_R$, and Vg is obtained by the equation:

$$Vg = a/d$$

wherein d represents the density of the gel.

Vt is obtained directly from the designing of the column. For the column according to the present invention, it is desirable that (Vi/Vo) be in the range of 1.0 to 2.0, preferably 1.2 to 1.8, in order to realize a harmonious combination of $W_R$ and Pd. For the column according to the present invention, it is essential in order to attain marked improvements to the chromatography speed, resolution and durability that the packing ratio (Pd) be in the range of 0.66 to 0.78, preferably 0.68 to 0.74, when (Vi/Vo) is in the range of 1.2 to 1.8. Meanwhile, to determine Vo, there is known a method in which a polymer having a larger molecular weight than the molecular weight exclusion limit is developed on the packed column and Vo is obtained as the peak volume of the eluate recorded on the chromatogram. This known method, however, is not recommended because it tends to bring about significant measuring errors under the influence of the molecular weight distribution of the developed polymer and the structure of the gel bed.

With respect to the column according to the present invention, detailed explanation will now be made. The gels used according to the present invention may be derived from a vinyl carboxylate polymer or copolymer. For example, the intended gels are obtained by subjecting to transesterification or saponification reaction in such a solvent as will not dissolve polyvinyl alcohol a totally porous homopolymer or copolymer from a single or a plurality of monomers containing at least two vinyl carboxylate groups, or a totally porous copolymer obtained by copolymerizing said monomer and a monomer containing a single vinyl carboxylate group, and then reacting the so obtained totally porous polyvinyl alcohol grains which substantially maintain the original fine pore structure with a cross-linking agent. For example, divinyl adipate is suspension-polymerized in water in the presence of a radical initiator, together with butyl acetate serving to make the resulting polymer porous. The resulting polymer is transformed to polyvinyl alcohol grains via a reaction in methanol to form hydroxyl groups. Then, the polymer grains are subjected to cross-linking reaction with epichlorohydrin in a mixture of acetone and dimethyl sulfoxide to obtain the intended gels. The details of the gels obtained according to the above-mentioned procedures were disclosed in Japanese Patent Application Laid- Open Specification No. 64657/1981 filed on Nov. 1, 1979.

Alternatively, the intended gels to be employed in the present invention may be obtained by copolymerizing a vinyl carboxylate monomer with a cross-linkable monomer, followed by transesterification reaction or the like. According to need, the polymer may be post-cured with epichlorohydrin or other cross-linking agent to obtain the intended gels. As examples of the cross-linkable monomer containing two or more ethylenically unsaturated groups, there can be mentioned a monomer having an isocyanurate ring, such as triallyl isocyanurate, a monomer having a cyanurate ring, such as triallyl cyanurate, and a divinyl ether, such as diethylene glycol divinyl ether. Of the above-mentioned monomers, triallyl isocyanurate is most preferred because it readily copolymerizes with vinyl carboxylate and the resulting gel has an excellent mechanical strength. For the gel from triallyl isocyanurate, the pore diameter and porosity are easy to control. The details of such gels and processes for preparation thereof were disclosed in Japanese Patent Application No. 85243/1980 (filed on June 25, 1980) and Japanese Patent Application No. 183703/1980 (filed on Dec. 26, 1980). For example, the intended gels may be obtained by suspension-copolymerizing triallyl isocyanurate and vinyl acetate mixed at an appropriate molar ratio, so that the degree of cross-linking may be of a predetermined value in the range of 0.20 to 0.40, in the presence of butyl acetate serving to make the polymer porous and a radical initiator, and then subjecting the so obtained totally porous copolymer to transesterification or saponification reaction in a methanol solution of NaOH. Any desired content of vinyl alcohol units in the polymer can be readily attained by controlling the conversion in the transesterification or saponification reaction. The above-mentioned degree of cross-linking (X) can be calculated according to the following formula:

$$X = \left(\frac{W_2}{M_2} \times 3\right) / \left(\frac{W_1}{M_1} + \frac{W_2}{M_2} \times 3\right)$$

wherein
$M_1$: Molecular weight of vinyl carboxylate,
$M_2$: Molecular weight of triallyl isocyanurate,
$W_1$: Weight of vinyl carboxylate used for polymerization,
$W_2$: Weight of triallyl isocyanurate used for polymerization.

In another aspect of the present invention, there is provided a process for preparing a liquid chromatography column comprising packing totally porous gels containing vinyl alcohol units in a wet state, characterized in that the process comprises the steps of:
(1) transferring a gel slurry into a packing apparatus detachably connected to a column having at its lower end a first end fitting equipped with a filter, which packing apparatus is then set in a pressurizable state;
(2) passing a liquid for packing through the packing apparatus and the column to move the gel slurry into the column while discharging the liquid entrained in the gel slurry and the liquid for packing through said filter of the first end fitting of the column, thereby forming a gel bed in the column;
(3) increasing the flow rate of the liquid for packing stepwise or continuously to adjust the packing ratio of the gel bed to a predetermined ratio; and
(4) detaching the column from the packing apparatus and attaching a second end fitting equipped with a filter to the column at its upper end, thereby to fix the formed gel into the colum;
in step (2) the liquid for packing being passed through the column at a flow rate of 0.2 to 1.5 m/hr from the beginning of feeding of the liquid for packing until the total volume of the passed liquid for packing reaches 1 to 300 times the internal volume of the column.

Packing of a gel slurry into a column may be done by the use of a pump according to the generally known wet packing process (see Hiroyuki Hatano, et al., "Experimental High-Speed Liquid Chromatography", published by Kagaku Dojin, Japan in 1977). According to the process of the present invention, it is of utmost importance not to impose an abrupt change of flow rate or pressure on the gel bed during the packing period. Any packing apparatus generally used in the art can be used according to the process of the present invention. In practicing the process of the present invention, a packer to pack the gel slurry into the column is usually connected to one end of the column. A liquid-transfer pipe from the elsewhere installed pump is also connected to the packer. The upper part of the packer is equipped with a shut-in device which can endure the pressure load during the packing period after pouring the gel slurry into the packer. On the end of the column from which the liquid is discharged, there is mounted a first end fitting equipped with a filter which permits passing of liquid but prevents passing of gel grains. According to need, an auxiliary column (generally known as "pre-column" in the art) having the same inside diameter as that of the main column may be fitted to the top and/or the bottom of the main column. The purpose of using said auxiliary column(s) is to improve the uniformity of gel bed by removing markedly nonuniform portions of the gel bed. The nonuniform portions of the gel bed tend to locate at both ends of the column, so that the nonuniform portions of the gel bed can be easily accomodated in the auxiliary column. Therefore, when the auxiliary column having the nonuniform portions of the gel bed accomodated therein is removed, the nonuniform portions are easily, completely removed together with the auxiliary column.

The gel slurry to be packed into the column according to the present invention may preferably be prepared by mixing gels in an amount of 1.1 to 4.0 times the quantity of the gels to be packed in the column with a dispersion medium, which is the same solvent as the liquid for packing to swell the gels. The slurry concentration may be suitably in the range of about 3 to about 30% by volume. Just before pouring the gel slurry into the packer, it is desirable to well disperse gels in the dispersion medium by means of ultrasonic waves or the like. After transferring the gel slurry into the packer, the whole packing apparatus is set in such a state as to be capable of enduring the pressure load during the packing period.

The step (2) above is a step for the transformation of gels in the form of a slurry to a packing bed of gels. It includes an improvement not seen in the prior art. Illustratively stated, the intra-column flow rate of the liquid for packing is maintained at 0.2 to 1.5 m/hr from the beginning of feeding of the liquid for packing until the total volume of the passed liquid for packing reaches 1 to 300 times the internal volume of the column in order to prevent a nonuniform gel bed from being formed in an early stage of the packing operation. If the flow rate of the liquid for packing is below 0.2 m/hr, not only the packing operation efficiency drops but a gel bed of too low a packing ratio results, which causes adverse effect on the quality stability necessary for the next step. If the flow rate of the liquid for packing exceeds 1.5 m/hr, a nonuniform gel bed as mentioned above tends to result. If the total volume of the passed liquid for packing is less than the internal volume of the column, a gel bed of an insufficient length is formed and, hence, a rapid movement of the remaining gel slurry into the column unfavorably occurs at the next step (3), causing the gel bed formed to be non-uniform. If the total volume of the passed liquid for packing exceeds 300 times the internal volume of the column, the packing operation efficiency disadvantageously becomes low.

The major purpose of the step (3) above is to obtain a high-performance column by increasing the packing ratio while maintaining the uniformity of the gel bed. In this step, the flow rate of the liquid for packing is increased stepwise or continuously. To attain the said purpose, the flow rate of the liquid for packing may be suitably increased so that the maximum pressure increase per meter of gel bed may be 60 $Kg/cm^2/min$ or less and the average pressure increase per meter of gel bed may be from 2 to 80 $Kg/cm^2/hr$. If the maximum pressure increase per meter of gel bed exceeds 60 $Kg/cm^2/min$, the uniformity of the gel bed may be impaired with increased probability. If the average pressure increase per meter of gel bed is below 2 $Kg/cm^2$, the packing operation efficiency decreases. If it exceeds 80 $Kg/cm^2$, a nonuniform gel bed disadvantageously tends to occur. The pressure increasing operation is stopped when the packing ratio of the gel bed has reached the intended value. According to need, thereafter, the liquid for packing is passed through the column for several hours at a flow rate which is not greater than the maximum flow rate that has been reached during the time of passing of the liquid for packing to give the intended packing ratio and at which no portion of the gel bed in the column is pushed back to the packer (usually, up to half the maximum flow rate) in order to stabilize the formed gel bed. Then, the main column is demounted from the packing apparatus, and the open end of the column is closed by means of a second end fitting having a filter of 2-10 μm pore diameter. The terminal point of the pressure increasing operation may be readily known referring to the previously obtained relationship between the maximum pressure or flow rate and packing ratio. Illustratively stated, the relationship between the maximum pressure or flow rate and the packing ratio may be obtained by a method in which multiple packed columns are first prepared by packing the columns at varied maximum pressures or varied maximum flow rates and the packing ratios of the packed columns are subsequently measured in accordance with the method as described hereinbefore. Adjusting of the packing ratio of the column according to the present invention can be readily attained by effecting packing of the column at the maximum pressure or flow rate corresponding to the predetermined packing ratio in reference to the above obtained relationship. As the liquid for packing, water or various aqueous solutions may be used. However, it is recommended that buffer solutions or aqueous solutions of organic and inorganic salts be used in a concentration not exceeding 1 mol/liter since such conditions as to bring about an excessive swelling of the gels as compared with swelling of the gels at chromatography should be avoided.

Preferred dimensions of the column according to the present invention are 4 to 50 mm in inside diameter and 100 to 600 mm in length. Tubes of stainless steel, glass, polyethylene or other material may be used, but a tube of most suitable material should be chosen in consideration of the kind of the eluent and the pressure imposed during the packing period of gels and at chromatography.

In practically utilizing the column according to the present invention, water, various buffer solutions and various aqueous solutions of organic and/or inorganic salts may suitably be used as the eluent. Nevertheless, the column may also be suitably utilized not only for the conventional partition chromatography in which a polar solvent is used, but also for the combined chromatography of gel permeation and partition in which there are used the above-mentioned aqueous solutions with an appropriate amount of an organic solvent added thereto.

In a further aspect of the present invention, there is provided a method of blood component analysis which comprises developing blood serum on a liquid chromatography column comprising a high packing ratio of gel bed of totally porous gels containing vinyl alcohol units and having an average grain diameter of 4 to 20 μm, and wherein the gel bed has a uniformity degree of 2.0 to 4.0, said uniformity degree being defined by HETP/Dp, in which HETP represents the height equivalent to a theoretical plate of the column and Dp represents the weight average grain diameter of the gels. The column according to the present invention is a high-performance liquid chromatography column capable of effectively separating various ionic and nonionic substances present in water or an aqueous solution of organic and/or inorganic salts. The present liquid chromatography column is especially useful for the separation of or the separation and identification of blood components for which there has been a strong demand in the art. When the separation of or the separation and identification of blood components according to the present invention are conducted, it is preferred that a column comprising the gels of a molecular weight exclusion limit (based on dextran) of 100,000 or more be used for the solutes having a molecular weight corresponding to albumin or more, that a column comprising the gels of a molecular weight exclusion limit (based on dextran) of 100,000 or less be used for the solutes having a molecular weight corresponding to albumin or less to about 100, that various buffer solutions, various aqueous solutions of organic and/or inorganic salts or mixtures thereof be used as eluent in a concentration of 0.05 to 0.5 mol/liter, and that an ultraviolet spectrophotometer be used as a detector.

As described above, the column according to the present invention and the process for preparing the same according to the present invention have collectively solved the hitherto encountered problems. In practice, they are of great advantage. Summing up the features of the present invention, the gels packed in the column according to the present invention contain nonionic vinyl alcohol units in the polymer skeleton, so that the adsorbability of solutes in an aqueous solution to the gels is low. Hence, it has become possible to conduct a direct analysis of blood serum or the like which has been difficult by means of partition chromatography or adsorption chromatography, so that data regarding blood components, often including that for their molecular weight can be obtained. According to the present invention, there can be provided a column comprising a uniform gel bed of a high packing ratio by a process in which a column is formed while avoiding imposing an abrupt change of flow rate or pressure on the gel bed during the column packing operation, thereby making it possible to simultaneously improve the velocity of elution and the durability of the column which has not been attained by means of the conventional aqueous-solvent GPC columns. Furthermore, the column according to the present invention comprises gels of small grain diameter, thereby exhibiting an improved separating capacity in addition to the above-mentioned advantages.

The present invention will be illustrated in more detail with reference to the following Examples, which should not be construed to be limiting the scope of the present invention.

EXAMPLE 1

A mixture of 80 g of divinyl adipate (having a purity higher than 99%), 200 g of n-butyl acetate, 6.4 g of polyvinyl acetate (having a polymerization degree of 500) and 1 g of 2,2'-azobisisobutyronitrile was suspension-polymerized at 70° C. for 20 hours in 1.2 liter of water containing 1% by weight of polyvinyl alcohol as a suspension stabilizer to obtain a poly (divinyl adipate). After completion of the polymerization, formed grains were recovered by filtration, washed with water and then with methanol and dried. The grains were charged in a 2 liter round-bottom flask together with 1 liter of methanol containing 32 g of sodium hydroxide, and the mixture was heated under agitation at 40° C. for 24 hours. After completion of the reaction, the resulting grains were recovered by filtration and washed with methanol and then with acetone.

The so obtained polyvinyl alcohol grains were charged in a round-bottom flask together with a liquid mixture comprising 350 ml of dimethyl sulfoxide, 350 ml of acetone, 37 g of epichlorohydrin and 16 g of sodium hydroxide, and the mixture was heated under agitation at 50° C. for 24 hours. After completion of the reaction, the grains were recovered by filtration and sufficiently washed with hot water and then with acetone. These filtration, washing and reaction operations were further repeated once more in the same manner as described above.

The resulting grains were heated at 80° C. for 24 hours under agitation together with a 1 N aqueous solution of sodium hydroxide, and the grains were sufficiently washed with water. The average diameter of the so obtained grains was determined by using "Coulter Counter Model ZB" (trade name of an apparatus manufactured and sold by Coulter Electronics Inc., U.S.A.). It was found that the average grain diameter was 12.3 $\mu$m. The $W_R$ value was 1.75 ml/g as determined according to the method described before. A part of the obtaned gels was reacted with acetic anhydride at 90° C. in a pyridine solvent and when the OH group concentraion ($q_{OH}$) in the gel was calculated from the amount of reacted acetic anhydride, it was found that the $q_{OH}$ value was 9.1 meq/g.

10 g (dry weight) of the so obtained grains was immersed overnight in 100 ml of distilled water and swollen. A first end fitting eqipped with a filter of 5 $\mu$m pore diameter was mounted on one end of a column of 7.5 mm in inside diameter and 500 mm in length, and the other open end of the column was connected to a packer of 100 ml in inside volumn. The paker is provided, at its upper portion, with an inlet of gel slurry, an inlet of a liquid for packing which is connected to a packing pump via a stainless pipe, and a pressure gauge. The packer can be sealed after a gel slurry is poured thereinto. The above-mentioned swollen gel slurry was subjected to sufficient dispersion for 10 min by means of an ultrasonic cleaning machine (BRANSON B-12 type manufactured and sold by Branson Cleaning Equipment Company, U.S.A.), and poured into the packer through the inlet of gel slurry. The packer was sealed. Then, distilled water (liquid for packing) was passed through the packer and column for 60 min at a flow rate of 1.0 ml/min [LV (linear velocity): 1.36 m/hr]. Thereafter, the flow rate of distilled water was increased at an average pressure increase rate of 20 Kg/cm$^2$/hr of gel bed and at a maximum pressure increase rate of 20 Kg/cm$^2$/min of gel bed until the pressure gauge indicated 85 Kg/cm$^2$. Distilled water was further passed for 3 hours while maintaining the gauge pressure at 85 Kg/cm$^2$ by controlling the quantity of distilled water fed from the pump. After stopping the passage of distilled water, the column was detached from the packer, and a second end fitting having the same structure as that of the first end fitting was mounted on the open end of the column. Thus, the packing of the column was completed. The obtained column exhibited a HETP/Dp value of 3.3, a Vi/Vo value of 1.54 and a molecular weight exclusion limit (based on dextran) of about 2,000,000.

Figure 2:
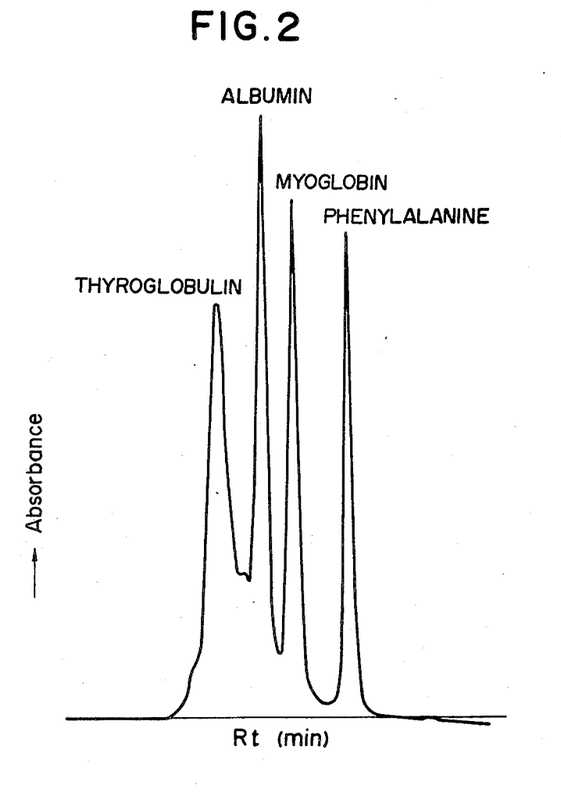
FIG. 2 is a chromatogram of a mixture of commercial thyroglobulin, albumin, myoglobin and phenylalanine (detected by UV absorption at 254 nm) obtained by using a liquid chromatography column according to Example 1 which will be given later.

An aqueous solution of commercial thyroglobulin, albumin, myoglobin and phenylalanine was developed on the above-obtained column, and eluted by a 0.05 mol/liter phosphoric acid buffer solution (pH 6.7) containing Na$_2$SO$_4$ in a concentration of 0.2 mol/liter at a flow rate of 1.0 ml/min. As is seen from the chromatogram of FIG. 2, the substances could be separated very effectively, flowing out in the order of molecular weights. The analysis time was about 20 min only.

EXAMPLE 2

A liquid mixture of 100 g of vinyl acetate, 32.2 g of triallyl isocyanurate (X-number: 0.25), 100 g of n-butyl acetate and 3.3 g of 2,2'-azobisisobutyronitrile was charged into a cylindrical flask having a capacity of 2 liters together with 0.8 liter of water containing 1% by weight of polyvinyl alcohol as a suspension stabilizer, and the resulting mixture was stirred to form a stable suspension. Then, the suspension was heated at 65° C. for 18 hours, and then at 75° C. for 5 hours under agitation to effect suspension polymerization. After completion of the polymerization, formed grains were recovered by filtration, washed with water and then with methanol and dried. The grains were charged in a round-bottom flask having a capacity of 3 liters together with 2 liters of methanol containing 47 g of sodium hydroxide, and the resulting mixture was heated under agitation at 15° C. for 20 hours to effect transesterification reaction. Thereafter, by conducting sedimentation classification in water, gels (Dp: 9.8 $\mu$m, Dp/Dn: 1.28) were obtained. The obtained gels exhibited a hydroxyl group concentration of 7.3 meq/g and a $W_R$ value of 1.58 ml/g.

Then, three 7 g (dry weight) portions were weighed out from the gels. Each of the three portions of gels was immersed overnight in 100 ml of a 0.2 mol/liter aqueous solution of $Na_2SO_4$, and dispersed for 5 min by means of an ultrasonic homogenizer (US-300 type, manufactured and sold by Nippon Seiki Seisakusho K.K., Japan). Each of the resulting gel slurries was poured into the packer which had been connected to a precolunn of 7.5 mm in inside diameter and 100 mm in length connected to one end of a stainless steel main column of 7.5 mm in inside diameter and 250 mm in length having at its other end a first end fitting equipped with a filter as used in Example 1, which precolumn and main column had been filled with an aqueous 0.2 mol/liter $Na_2SO_4$ solution. After sealing the packer, an aqueous 0.2 mol/liter $Na_2SO_4$ solution (liquid for packing) was passed through the packer and precolumn and main column at a flow rate of 0.5 ml/min (LV: 0.68 m/hr) for 60 min by operating the pump. During that period, the gel slurry was removed into the main column while dicharging the aqueous 0.2 mol/liter $Na_2SO_4$ solution entrained in the gel slurry and that used as the liquid for packing through the first end fitting mounted on the lower end of the main column, thus forming a gel bed in the main column. Thereafter, the flow rate of aqueous 0.2 mol/liter $Na_2SO_4$ was gradually increased at an average pressure increase rate of 5 $Kg/cm^2/hr$ of gel bed and at a maximum pressure increase rate of 5 $Kg/cm^2/min$ of gel bed until the pressure gauge mentioned in Example 1 indicated 26, 46 or 57 $Kg/cm^2$. While maintaining the reached pressure, the liquid for packing was continued to be passed through the columns for further 2 hours. Thereafter, the packer and the precolumn were demounted, and a second end fitting was attached to each column to fix the gel bed.

These columns were inspected with respect to the characteristic properties and practical performance to give favorable results. The characteristic properties of these columns, which are of importance according to the present invention, are shown in Table 1.

TABLE 1

| Column No. | HETP/Dp | Vi/Vo | Pd |
|---|---|---|---|
| 1 | 2.95 | 1.34 | 0.67 |
| 2 | 2.30 | 1.61 | 0.71 |
| 3 | 3.34 | 1.90 | 0.74 |

All these columns had a molecular weight exclusion limit (based on dextran) of about 30,000.

On the column No. 1 was developed a mixture of commercial γ-globulin, albumin from bovine blood serum, albumin from egg white and myoglobin, and elution was conducted using a pH 7.0 aqueous solution of 0.3 mol/liter NaCl and 0.1 mol/liter sodium phosphate as eluent. Every component was recovered by nearly 100%. All of these proteins flowed out in the order of molecular weights.

On the column No. 2 was developed 100μ liter (1 mg) of aqueous 1% by weight ethylene glycol, and elution was conducted with distilled water at 15° C. at a flow rate of 1.0 ml/min. From the obtained chromatogram, HETP was determined. This procedure was repeated 800 times. HETP values were in the range of 24.5 to 25.6 μm. The stability of HETP values can be considered as demonstrating the prolonged durability of the column and non-occurrence of any degradation thereof.

Through the column No. 3 was continuously passed aqueous 0.2 mol/liter $Na_2SO_4$ at a flow rate of 1.2 ml/min for 240 hours, whereupon HETP was determined to show a favorable value of 32.9 μm (HETP/Dp=3.36). No degradation of the column was observed.

EXAMPLE 3

Figure 3A:
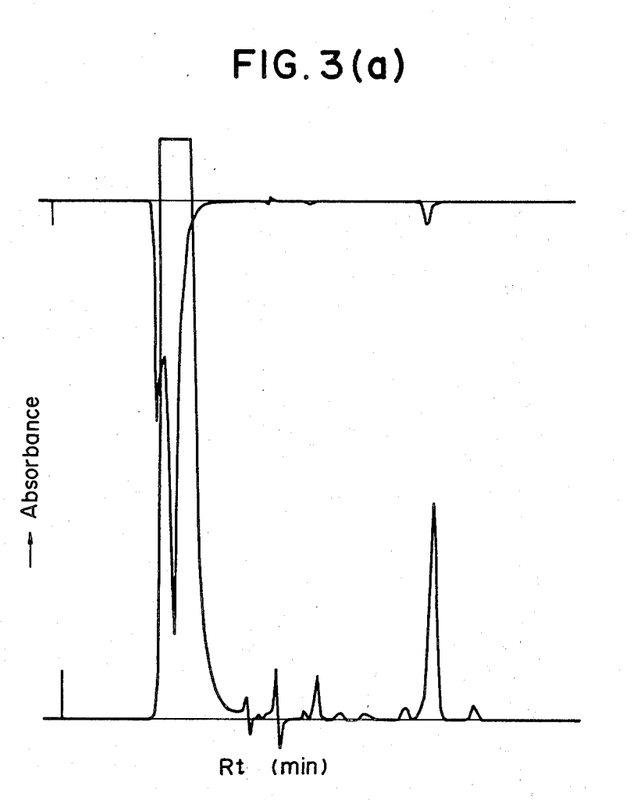
Figure 3B:
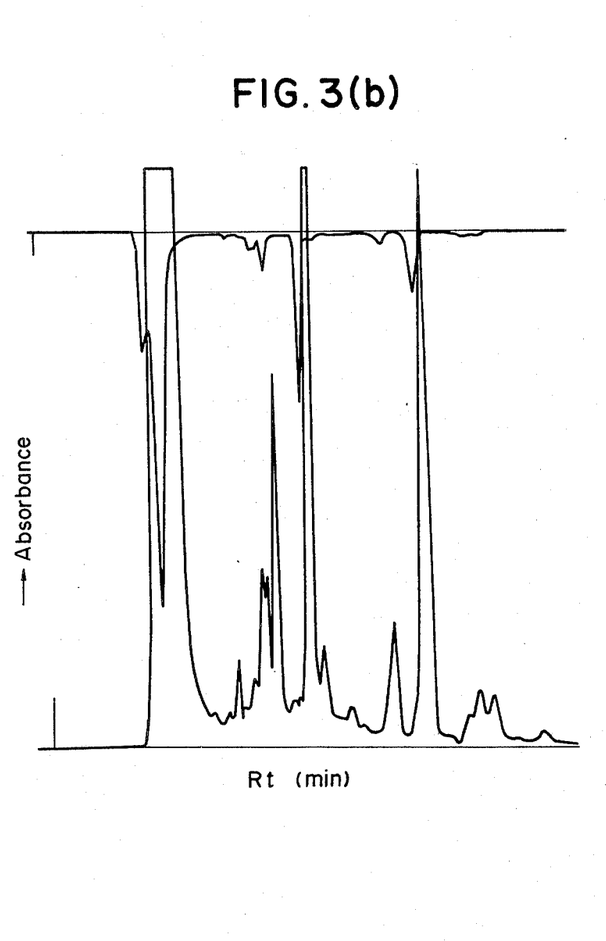

Human serum was developed on the connected column No. 1 and column No. 2 which were prepared according to Example 2, and eluted by a pH 7.0 aqueous solution of 0.3 mol/liter NaCl and 0.1 mol/liter sodium phosphate at a flow rate of 1.0 ml/min using an ultraviolet spectrophotometer at 250 nm (wave length) as detector. FIG. 3(a) shows a chromatogram of a normal human serum obtained according to the above procedure, and FIG. 3(b) shows a chromatogram of a renal failure serum. On the same chart, two chromatograms, which were obtained by varying the sensitivity of the detector, are given to jointly indicate the major and minor components of the serum. From these chromatograms, it can be concluded that the liquid chromatography column according to the present invention has an excellent resolution of substances, and that it is especially useful for fractionating mixtures containing many kinds of solutes, such as blood.

COMPARATIVE EXAMPLE 1

Figure 4:
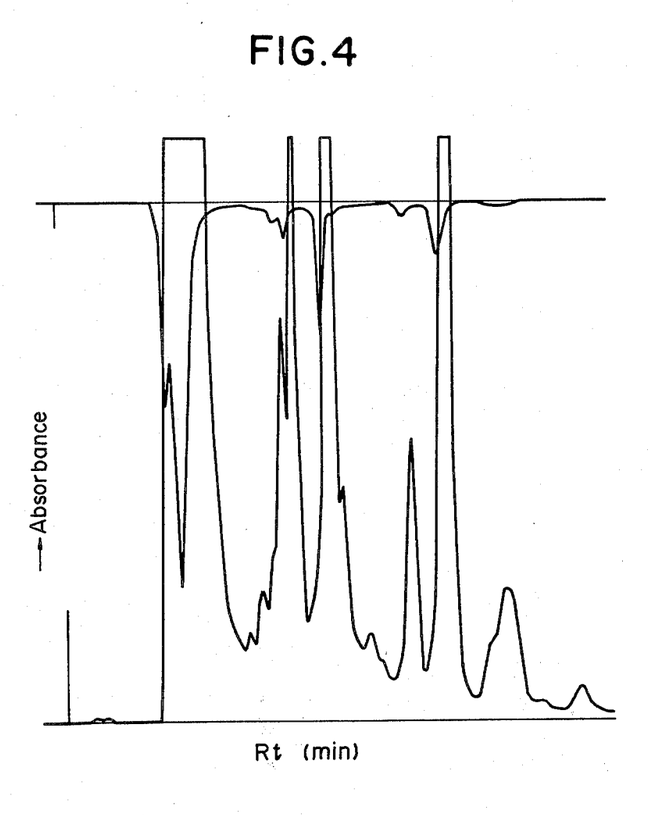
FIG. 4 is a chromatogram obtained by fractionating the renal failure serum (detected by UV absorption at 254 nm) according to Comparative Example 1 which will be given later.

From the gels obtained according to Example 2 was weighed out 10 g of gels, which was subjected to the same swelling and dispersion operation as in Example 2 and then put into the packer connected with a column of 7.5 mm in inside diameter and 500 mm in length. Keeping the pressure at the entrance of the column at 70 $Kg/cm^2$, the gel slurry was transferred into the column. The liquid for packing was passed through the column for 4 hours, while maintaining the said pressure. Thereafter, a second end fitting was attached to the packed column to fix the gel bed. The obtained column had a HETP/Dp value of 7.1. By using this column, chromatography was conducted for the same sample (serum from a patient suffering from renal failure) as employed in Example 3 under the same conditions as employed in Example 3. FIG. 4 shows the obtained chromatogram. By comparing FIG. 4 and FIG. 3(b), it can be concluded that the packed column according to the present invention has much greater resolution than that obtained in this Comparative Example 1.

EXAMPLE 4

A mixture of 100 g of vinyl acetate, 41.4 g of triallyl isocyanurate, 70 g of n-butyl acetate and 3.3 g of 2,2'-azobisisobutyronitrile was charged into a flask, and suspension-polymerization, transesterification and classification were performed in substantially the same manner as in Example 2 to obtain gels having a Dp value of 9.4 μm. The gels had a hydroxyl group concentration of 7.1 meq/g and a $W_R$ value of 1.20 ml/g. 13 g was weighed out from the gels, and packed into a stainless steel column of 7.5 mm in inside diameter and 500 mm in length in the same manner as in Example 1 to obtain a packed column which had a HETP/Dp value of 2.75 and a Vi/Vo value of 1.55.

Figure 5A:
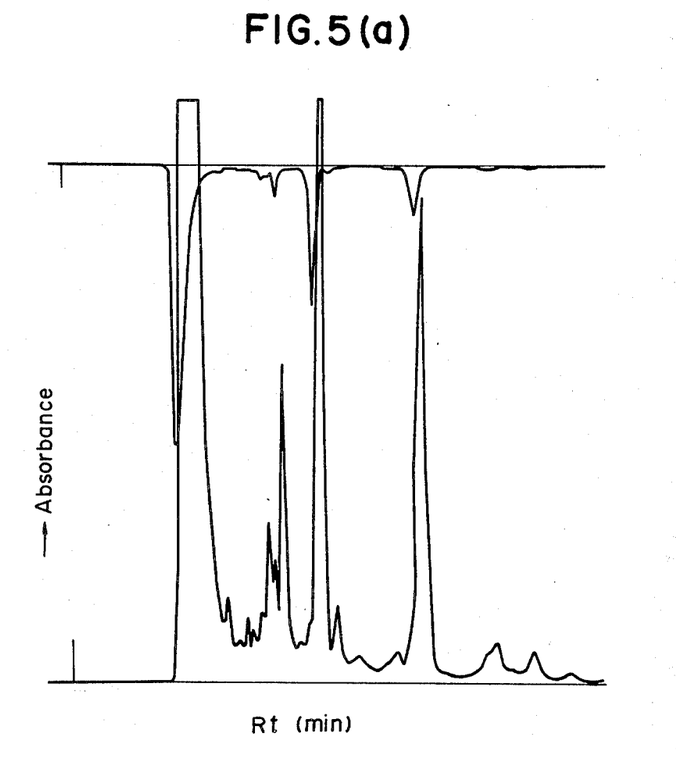
Figure 5B:
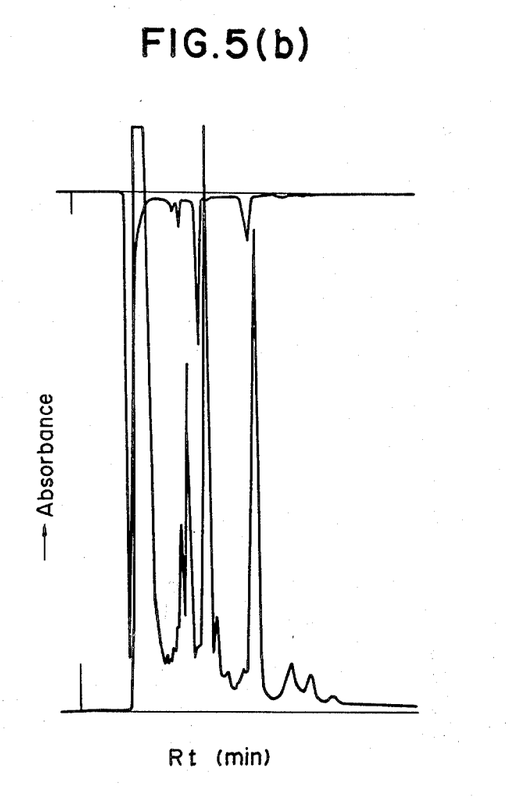

Using this column, chromatography was effected for serum from a patient suffering from renal failure in substantially the same manner as in Example 2, except that the analysis was conducted at a greater flow rate of eluent as well. FIG. 5(a) shows a chromatogram obtained at a flow rate of eluent of 1.0 ml/min, and FIG. 5(b) shows a chromatogram obtained at a flow rate of eluent of 2.0 ml/min. The chromatogram [FIG. 5(b)] obtained at such a high flow rate of eluent as 2.0 ml/min, which is 2.72 m/hr in terms of linear velocity, demonstrates nearly as high a resolution as that [FIG. 5(a)] obtained at a flow rate of eluent of 1.0 ml/min. Therefore, it can be concluded that the packed column according to the present invention ensures high-speed, high-resolution chromatography. In addition, even after being used for chromatography of 150 samples of blood serums at a flow rate of 2.0 ml/min, the column maintained the initial resolution and efficiency that was exhibited upon preparation thereof. This evidences the prolonged durability of the packed column according to the present invention.

EXAMPLE 5

Figure 6:
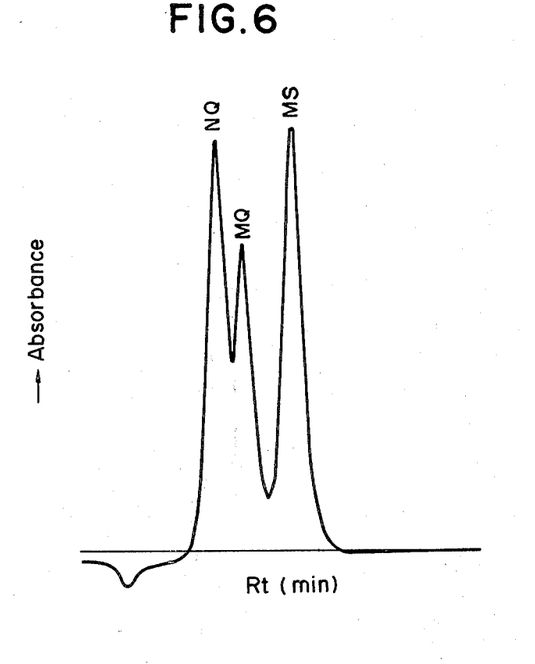
FIG. 6 is a chromatogram of a mixture (detected by UV absorption at 254 nm) formed in the course of the process of producing an agricultural chemical which was obtained by using the liquid chromatography column according to Example 5 which will be given later.

A mixture of 100 g of vinyl acetate, 32.3 g of triallyl isocyanurate (degree of crosslinking: 0.25), 40 g of n-butyl acetate and 3.3 g of 2.2'-azobisisobutyronitrile was suspension polymerized, filtered, extracted, transesterified and classified in substantially the same manner as described in Example 2 to obtain gels having a Dp value of 13 $\mu$m, a Dp/Dn value of 1.32, a hydroxyl group concentration of 8.2 meq/g and a $W_R$ value of 1.05 ml/g. The so obtained gels were packed into a column of 7.5 mm in inside diameter and 500 mm in length in substantially the same manner as in Example 1 to obtain a packed column of HETP/Dp 3.4 and Vi/Vo 1.20. Using this packed column, chromatography was effected for an aqueous mixture of chlorides of N,N'-dimethyl-4,4'-bipyridylium(NQ), N-methyl-4-(4-pyridyl)-pyridinium(MQ) and N-methylpyridinium(MS), which mixture was produced in the course of preparing an agricultural chemical, by eluting with aqueous 0.3 mol/liter NaCl at a flow rate of 1.0 ml/min. The resulting chromatogram is shown in FIG. 6. It clearly shows fractions of the mixture. From this, it can be concluded that the packed column according to the present invention is also effectively applicable to fractionating and identifying low molecular weight electrolytes.

What is claimed is:

1. A liquid chromatography column comprising a high packing ratio of gel bed of a totally porous polymer containing vinyl alcohol units and having a weight average grain diameter of 4 to 20 $\mu$m, and wherein the bed has a uniformity degree of 2.0 to 4.0, said uniformity degree being defined by HETP/Dp in which HETP represents the height equivalent to a theoretical plate of the column and Dp represents the weight average grain diameter of the polymer.

2. A liquid chromatography column according to claim 1, wherein the polymer has a weight average diameter of 6 to 15 $\mu$m.

3. A liquid chromatography column according to claim 1, wherein the polymer is a vinyl carboxylate homopolymer or copolymer.

4. A liquid chromatography column according to claim 3, wherein the copolymer is a copolymer of vinyl carboxylate and a cross-linkable monomer containing an isocyanurate ring.

5. A liquid chromatography column according to claim 3, wherein the copolymer is a copolymer of vinyl carboxylate and a cross-linkable monomer containing an cyanurate ring.

6. A liquid chromatography column according to claim 4, wherein the cross-linkable monomer containing the isocyanurate ring is triallyl isocyanurate.

7. A liquid chromatography column according to claim 3, wherein the vinyl carboxylate homopolymer or copolymer is prepared from a monomer containing at least two ester groups of vinyl carboxylate.

8. A liquid chromatography column according to claim 7, wherein the monomer containing at least two ester groups of vinyl carboxylate is divinyl adipate.

9. A liquid chromatography column according to claim 1, wherein the polymer has a water regain value of 0.6 to 2.0 ml/g and a Vi/Vo value, in which Vi represents the inner volume within the gel grain and Vo represents the void volume between the gel grains, of 1.0 to 2.0.

10. A liquid chromatography column according to claim 1, wherein the polymer has a hydroxyl group concentration of 3 to 15 meq/g.

11. A liquid chromatography column according to claim 1, wherein the polymer has a packing ratio of 0.66 to 0.78.

12. A process for preparing a liquid chromatography column comprising packing a gel of totally porous polymer containing vinyl alcohol units in a wet state, characterized in that the process comprises the steps of:
(1) transferring a gel slurry of a totally porous polymer into a packing apparatus detachably connected to a column having at its lower end a first end fitting equipped with a filter, which packing apparatus is then set in a pressurizable state;
(2) passing a liquid for packing through the packing apparatus and the column to move the gel slurry into the column while discharging the liquid entrained in the gel slurry and the liquid for packing through said filter of the first end fitting of the column, thereby forming a gel bed in the column;
(3) increasing the flow rate of the liquid for packing stepwise or continuously to adjust the packing ratio of the gel bed to a predetermined ratio; and
(4) detaching the column from the packing apparatus and attaching a second end fitting equipped with a filter to the column at its upper end, thereby to fix the formed gel into the column;
(in step 2) the liquid for packing being passed through the column at a flow rate of 0.2 to 1.5 m/hr from the beginning of feeding of the liquid for packing, until the total volume of the passed liquid for packing reaches 1 to 300 times the internal volume of the column.

13. A process for preparing a liquid chromatography column according to claim 12, wherein in step (3) the flow rate of the liquid for packing is increased so that the maximum pressure increase per meter of gel bed may be 60 Kg/cm$^2$/min or less and the average pressure increase per meter of gel bed may be from 2 to 80 Kg/cm$^2$/hr.

14. A process for preparing a liquid chromatography column according to claim 12, wherein the polymer has a weight average grain diameter of 4 to 20 $\mu$m.

15. A process for preparing a liquid chromatography column according to claim 12, wherein the column has an inside diameter of 4 to 50 mm and a length of 100 to 600 mm.

16. A process for preparing a liquid chromatography column according to claim 12, wherein the polymer is a copolymer of vinyl carboxylate and triallyl isocyanurate.

17. A process for preparing a liquid chromatography column according to claim 12, wherein the gel slurry has a gel content of 1.1 to 4 times the gel quantity to be packed in the column.

18. A method of blood component analysis which comprises developing blood serum on a liquid chromatography column comprising a high packing ratio of gel bed of a totally porous polymer containing vinyl alcohol units and having a weight average grain diameter of 4 to 20 μm, and wherein the gel bed has a uniformity degree of 2.0 to 4.0, said uniformity degree being defined by HETP/Dp, in which HETP represents the height equivalent to a theoretical plate of the column and Dp represents the weight average grain diameter of the polymer.

* * * * *